United States Patent [19]

Fleming et al.

[11] Patent Number: 4,923,162
[45] Date of Patent: May 8, 1990

[54] RADIATION SHIELD SWIVEL MOUNT

[76] Inventors: Matthew C. Fleming, 751 Smith Ave., Pinole, Calif. 94564; Melvin T. Magliocco, 156 Greenwood Ave., San Rafael, Calif. 94901

[21] Appl. No.: 245,700
[22] Filed: Sep. 19, 1988
[51] Int. Cl.⁵ .............................................. F16C 11/06
[52] U.S. Cl. .................................. 248/276; 248/288.3; 248/481
[58] Field of Search .................... 248/276, 288.3, 481, 248/181, 663; 403/165, 133, 132, 141, 115, 114

[56] References Cited

U.S. PATENT DOCUMENTS

| | | | |
|---|---|---|---|
| 357,337 | 2/1887 | Rosenblatt | 403/133 X |
| 815,947 | 3/1906 | Fergusson | 403/114 |
| 2,328,135 | 8/1943 | Gack | 248/276 X |
| 3,392,950 | 7/1968 | Pierce | 248/481 X |
| 3,409,317 | 11/1968 | Richards | 403/115 X |
| 3,498,579 | 3/1970 | Vicary | 248/481 X |
| 3,968,975 | 7/1976 | Herbenar | 403/114 X |
| 4,142,816 | 3/1979 | Kramer | 403/141 |

*Primary Examiner*—Ramon S. Britts
*Assistant Examiner*—Karen J. Chotkowski
*Attorney, Agent, or Firm*—Bruce & McCoy

[57] ABSTRACT

A swivel mount for a radiation shield having a bearing mounted at the end of a support arm with the bearing engaged to the shield between clamping members proximate the balance center of the radiation shield whereby the shield can be positioned at variable orientations.

3 Claims, 1 Drawing Sheet

U.S. Patent
May 8, 1990
4,923,162
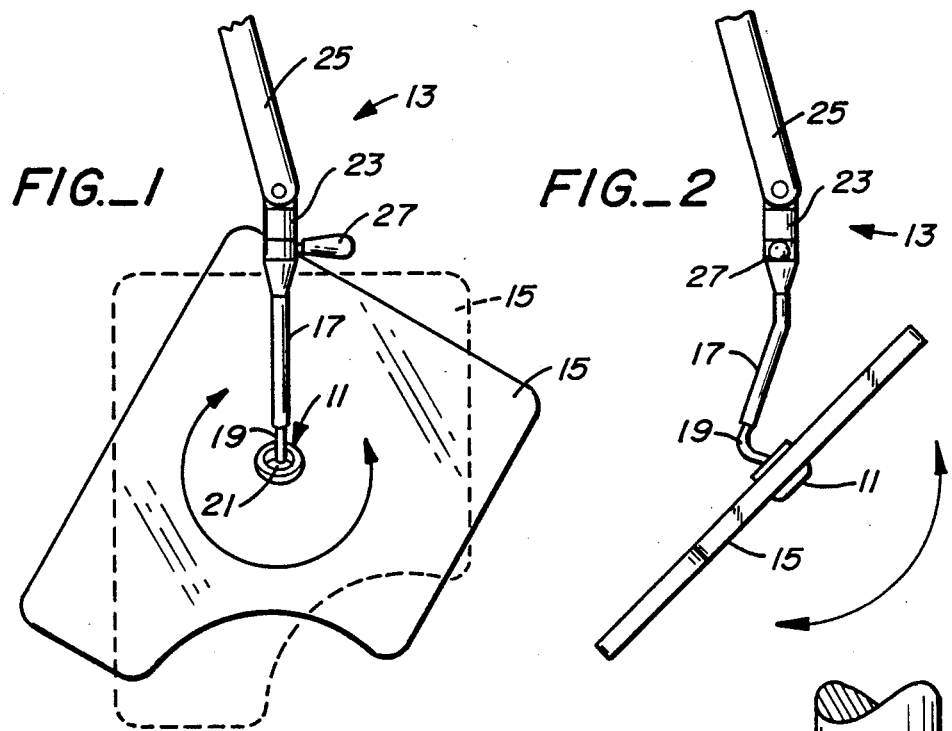
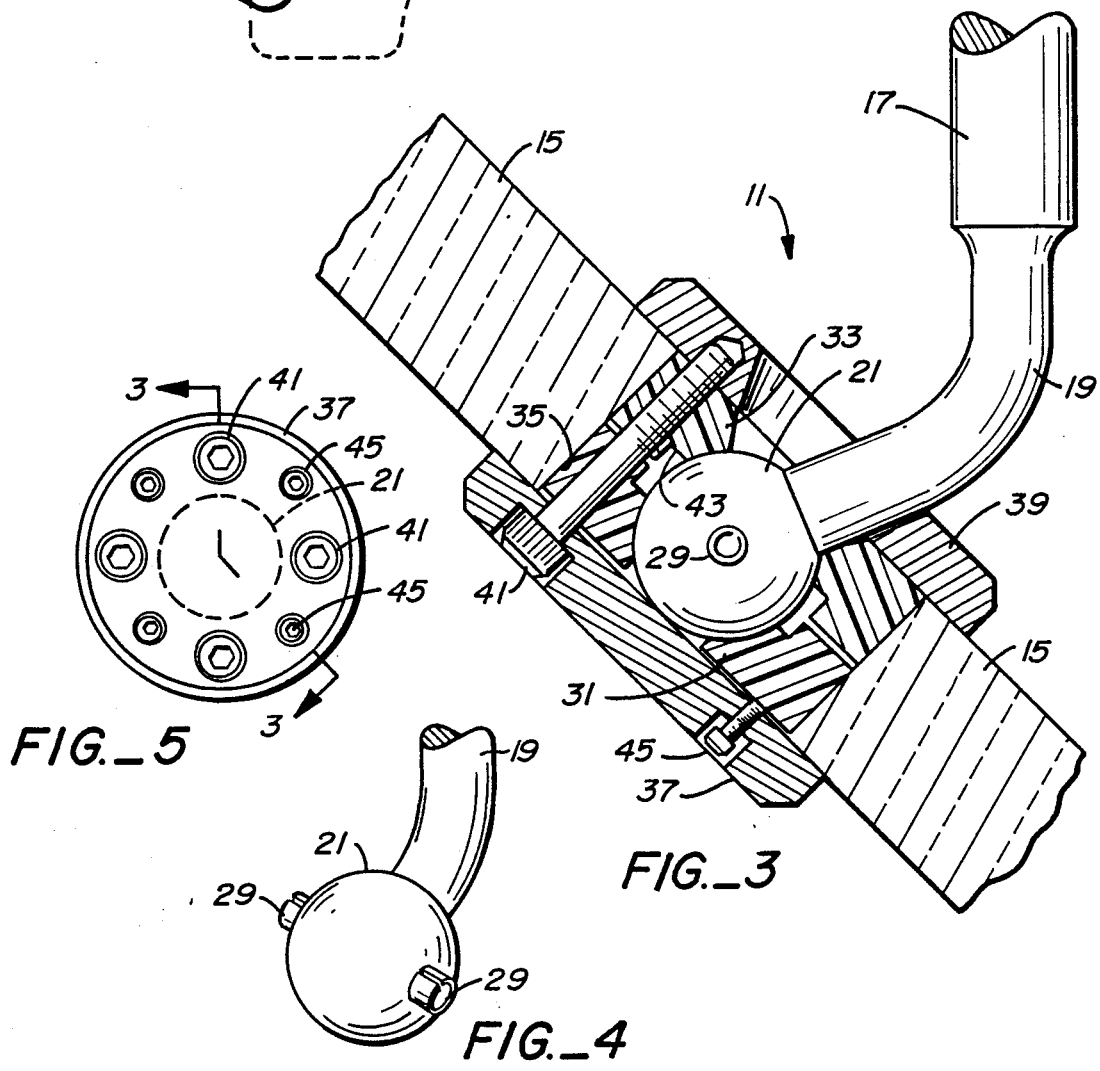

4,923,162

RADIATION SHIELD SWIVEL MOUNT

BACKGROUND OF THE INVENTION

1. Field Of The Invention

The present invention relates to means for supporting radiation shields and more particularly to a swivel mount for a radiation shield which engages the shield at the balance center by a single attachment point whereby the shield can be positioned at variable orientations.

2. Description Of The Prior Art

Radiation shields have long been used by hospitals and medical clinics for the purpose of shielding that portion of a patient's body which does not need to be exposed to the radiation produced by the examination or treatment machine. More recently procedures are requiring the presence of physicians to attend the patient and observe the progress of the examination or procedure, and they are thus exposed to secondary radiation and need to be protected by radiation shields. These shields have taken many forms, but in recent years a preferred form is formed of a leaded glass or leaded plastics which allows visibility of the patient through the shield by the doctor or the technician who is positioning the shield. The problem in positioning these leaded glass shields is that they are very heavy, and the weight problem is exacerbated by the need for heavy frames which surround the leaded glass to provide mounting supports for the shield. The supports have usually utilized attachment points somewhere on the frame, most usually on both sides of the frame, for the purpose of allowing the frame to be pivoted forward and backward and to be rotated around a vertical axis. In some designs the frame of the shield is gripped from the top at a single attachment point, but this design has very limited orientation capability due to gravity which tends to orient the weight of the frame and shield in a substantially vertical alignment.

SUMMARY OF THE INVENTION

The present invention provides a design for a radiation shield mount or support which eliminates the frame of the shield and allows the shield to be suspended or supported by a single attachment point at the balance center of the shield to allow variable orientation of the shield. It is a swivel mount for a radiation shield which is comprised of a support arm having a bearing member mounted at the end of the arm. An opening is formed in the shield proximate the balance center thereof and a pair of clamping members are disposed on opposite sides of the shield and interlocked together. The bearing member of the support arm is captured between the clamping members. Bearing pads are mounted between the clamping members on opposite sides of the bearing member and contact the bearing member with a variable pressure friction engagement whereby the shield can be partially rotated with respect to the bearing member and the shield thereby positioned at variable orientations within the limits of rotation of the shield on the bearing member.

OBJECTS OF THE INVENTION

It is therefore an important object of the present invention to provide a swivel mount for a radiation shield which eliminates the need for a frame for said shield and engages the shield near its balance center.

It is another object of the present invention to provide a swivel mount for a radiation shield which allows the shield to be positioned at variable orientations with respect to a patient's body without the need for counterbalancing the changes of the shield's orientation.

It is a further object of the present invention to provide a radiation shield which is secured to its support arm with a variable pressure friction engagement whereby it will maintain predetermined angulated orientations.

It is still another object of the present invention to provide a swivel mount for a radiation shield which provides for substantial variations in orientation of said shield which includes 360 degree rotation of said shield around its attachment to its support arm; 360 degree rotation around the vertical axis; and angulation between the vertical and approximately 45 degrees to the horizontal.

Other objects of the present invention will become apparent when the description of the preferred embodiment thereof is considered in conjunction with the accompanying drawings.

BRIEF DESCRIPTION OF THE DRAWINGS

FIG. 1 is a side elevation of the upper sections of the support arm as used with the present invention and a rear elevation of the lower end support arm and swivel mount of the present and of the radiation shield;

FIG. 2 is a side elevation of all the support arms and the swivel mount of the present invention and of the radiation shields;

FIG. 3 is a partial cross-section in side elevation of the swivel mount of the present invention;

FIG. 4 is a broken out perspective view of the end of the support arm and bearing member of the preferred embodiment of the present invention; and FIG. 5 a front elevation of the front clamping member of the present invention.

DESCRIPTION OF THE PREFERRED EMBODIMENT

The present invention is a swivel mount 11 and support arm 13 for a radiation shield 15 which permits the shield to be supported by a single attachment point near its balance center. It is desirable in most radiation treatment or examination rooms to support radiation shields from the ceiling to leave the floor unobstructed for operator and patient movement and for ease of floor cleaning and the preservation of cleanliness. The shield must yet be provided with a wide range of movement to permit it to be stored out of the way during periods of non-use and while the patient is being positioned in the treatment or examination area and to permit it to be easily moved into the working area proximate the focus of the treatment or examination machine.

These objectives have been accomplished for a period of time by the use of articulating arms mounted on the wall or ceiling which are spring loaded or counterweighted to support the weight of the radiation shield. This support arrangement can be utilized for the present invention, but it utilizes a specifically configured vertically depending terminus or end arm 17 on the articulated support arm 13. The configured shape of the vertically depending end arm 17 includes an angled off-set 19 at the lower end thereof which terminates in a bearing member 21. The configured shape of the end arm 17 places the bearing member 21 at the center of gravity of the radiation shield and directly below the connection 23 of the depending end arm section 17 with the adjacent intermediate section 25 of the articulated support arm 13. The connection 23 between the end arm section 17 and the adjacent support arm section 25 is a rotatable bearing which allows the vertically depending end arm 17 to rotate 360 degrees around the vertical axis. A short handle 27 can be provided at the top end of the vertically depending end arm section 17, proximate the rotatable bearing 23, to assist in rotating the shield 15 around the vertical axis.

In the preferred embodiment of the invention, the bearing member of the swivel mount 21 is basically spherical in shape except for an intersecting pin 29 and except where the bearing engages the support arm with a threaded or welded connection. The pin 29 which intersects the bearing member 21 is preferably cylindrical in shape, in its preferred form, and is disposed horizontally and perpendicular to the axis of the end of the support arm 17. The pin 29 restricts movement of the shield 15 on the bearing member 21 as will become apparent when the bearing pads 31, 33 which engage the bearing member 21 are considered hereinafter. The bearing member of the swivel mount could be other configurations such as cylindrical and serve as well as the preferred embodiment, but the assembly would most likely be more expensive to manufacture.

An opening 35 is formed in the radiation shield proximate the balance center thereof, and the bearing member 21 of the support arm 17 is disposed in the center of that opening in its operative position. The preferred form of the opening is circular as that configuration allows accurate machining of the bearing pads 31, 33 which fit in the opening and engage the bearing member 21.

A pair of clamping members 37, 39 are disposed on opposite sides of the shield 15 and are interlocked together thereby clamping the bearing member 21 on the support arm 17 therebetween. The clamping members 39 includes an opening through which the support arm 17 projects to its engagement with the bearing member 21 disposed between the clamping members 37, 39. The clamping members are interlocked in the preferred embodiment by tie bolts 41 which extend through the bearing pads 31, 33. The bearing pads, by virtue of their fit in the opening 35 in the shield, center the clamping members on the opening.

The bearing pads 31, 33 which are mounted in the opening 35 in the shield 15 are trapped between the clamping members 37, 39 on opposite sides of the bearing member 21 and contact the bearing member with an adjustable pressure friction engagement. The friction engagement permits the shield to be partially rotated on the bearing member between limits whereby the shield can be positioned at variable predetermined orientations within the limits of rotation of the shield on the bearing member. The bearing pads 31, 33 are formed with an internal cavity 43 in the configuration of a flat cylinder or disk which permits the pin 29 which extends through the bearing member 21 to rotate 360 degrees between the bearing pads 31, 33 when the shield 15 is rotated around the bearing Angulation of the shield is limited by the cylindrical pin 29 to partial rotation around the axis of the pin and by the rear clamping member 39 which encircles the end of the support arm. The angulation is essentially from the vertical to about 45 degrees from the horizontal.

The bearing pads 31, 33 are provided with means to vary the pressure engagement of the pads with the bearing member 21. This is effected in the preferred embodiment by providing adjustment screws 45 which project through either of the clamping members 37, 39 to engage the adjacent bearing pad and force it towards the bearing member. The front clamping member 37, without an opening formed therein for the support arm, is the most appropriate as it provides more surface area to work with and is easier to approach or access for adjustment.

The bearing pads include at least one ring bearing pad 33 mounted in the opening 35 of the shield 15 adjacent the rear clamping member 39 which is the one formed with an opening. At least a partially concave adjustable bearing pad 31 is mounted adjacent the front clamping member 37, and opposed to said ring bearing pad 33, on the opposite side of said bearing member 21. In the preferred embodiment, the concave pad 31 is also a ring bearing pad provided with an adjustable fit whereby it can be moved towards and away from the bearing member 21 to change the pressure or friction on the bearing member in response to the tightening or loosening of the adjustment screws 45 projecting through the front clamping member 37. As a result, the radiation shield 15 can be translated to variable orientations and yet the shield will maintain those orientations once the shield has been positioned due to the friction caused by the bearing pads 31, 33 on the bearing member 21. Due to the fact that the swivel mount 11 is located in the preferred embodiment at the balance center of the shield 15, and under the rotatable connection 23 of the support arms 17, 25, the shield is self-counterbalancing and needs little or no external force to counterbalance changes in orientation. The friction engagement of the bearing member is provided to prevent inadvertent movement of the shield by external forces not sufficient to overcome the friction engagement.

To operate the present invention, the shield is first moved from its storage position to the operative position proximate the patient. The shield is usually next, or concurrently with movement from the storage position, rotated around the vertical axis. The shield is then positioned with respect to the patient by rotation of the shield about the bearing and angulation of the shield with respect to the horizontal. The weight of the shield is counterbalanced by the support arms 13, so the only effort required to position the shield by the operator is that to overcome the support arm residual resistance and the friction engagement of the shield with the bearing member, the latter of which can be varied by the operator.

Thus it will be seen, from this description of the preferred embodiment of the present invention, that the swivel mount and support arm for a radiation shield disclosed and described herein achieves the objects and advantages attributable thereto, and while the invention has been described in considerable detail, it is not to be limited to such details as have been set forth except as may be necessitated by the appended claims.

We claim:

1. A swivel mount for a radiation shield comprising an articulated support arm having at least two joined arm sections with one of said sections being a configured end arm section which is rotatably connected to the other arm section and hangs downward therefrom with an angled off-set at the lower end thereof which terminates in a substantially spherical bearing member which is disposed to hang vertically under the connection of said arm sections, said bearing member including a horizontal pin member extending through the center of said bearing member perpendicular to the longitudinal axis of a cantilevered end of said end arm section where said end arm section engages said bearing member, a radiation shield having a circular opening formed proximate the balance center thereof, a pair of clamping members disposed on opposite sides of the opening formed in said shield and trapping said bearing member of said end arm section therebetween, one of said clamping members having an aperture formed therein through which the support arm projects, said clamping members being interlocked by tie bolts, and bearing pads mounted between said clamping members and contacting said bearing member on opposite sides thereof with a variable pressure friction fit whereby said bearing can be partially rotated with respect to said clamping members and said shield can be positioned at variable orientations within the limits of rotation and angulation of said shield on said bearing member, said bearing pads being formed to provide a cavity to accommodate said pin which permits the shield to be rotated 360 degrees around said bearing member and said pin.

2. A swivel mount for a radiation shield comprising a support arm having a bearing member mounted at the end thereof, said bearing member being spherical in shape except where said bearing member engages said support arm, said bearing member including a horizontally disposed pin member extending through the center of said bearing member perpendicular to the longitudinal axis of the cantilevered end of said support arm where said support arm engages said bearing member, a radiation shield having an opening formed proximate the balance center thereof, a pair of clamping members disposed on opposite sides of said shield and interlocked together clamping the shield and the bearing member of said support arm therebetween in said opening, and bearing pads mounted between said clamping members on opposite sides of said bearing member and capturing said bearing member therebetween with friction engagement whereby said shield can be partially rotated with respect to said bearing member and positioned at variable stable orientations within the limits of rotation of said shield on said bearing member, said bearing pads including a ring bearing pad mounted concentric with the opening of said clamping member and having an aperture, and at least a partially concave adjustable bearing pad mounted adjacent said other clamping member opposed to said ring bearing pad on the opposite side of said bearing member, said bearing pads being formed to provide a cavity to accommodate said pin member which permits the shield to be rotated 360 degrees around said bearing member and said pin.

3. The swivel mount of claim 2 wherein said support arm is articulated by means of at least two jointed arm sections with the end arm section which terminates in said bearing member having a configured vertically depending section with an angled off-set at the lower end thereof terminating in said bearing member with said bearing member being vertically disposed under the connection of the arm sections, said vertically depending section of said arm being rotatable around the vertical axis.

* * * * *